United States Patent [19]

Futekov et al.

[11] Patent Number: 4,494,871
[45] Date of Patent: Jan. 22, 1985

[54] DEVICE FOR PULSE DOSAGE OF LIQUID MICROSAMPLES INTO THE FLAME OF ATOM ABSORPTION SPECTROPHOTOMETER

[75] Inventors: Lyubomir P. Futekov; Georgi L. Bekyarov; Rina G. Parichkova, all of Plovdiv, Bulgaria

[73] Assignee: Nauchno-Proizvodstveno Predpriyatie "Balkan", Plovdiv, Bulgaria

[21] Appl. No.: 322,544

[22] Filed: Nov. 18, 1981

[51] Int. Cl.³ .............................................. G01N 21/72
[52] U.S. Cl. ...................................... 356/315; 422/82
[58] Field of Search ............... 356/312, 315, 316, 417, 356/311; 422/36, 54, 80, 82

[56] References Cited

U.S. PATENT DOCUMENTS 3,625,614 12/1971 Herrmann et al. ................... 356/311
4,212,845 7/1980 Stelling et al. ......................... 422/82

FOREIGN PATENT DOCUMENTS 52-34774 3/1977 Japan ................................... 356/440
1098425 8/1965 United Kingdom .
1157953 11/1966 United Kingdom .
1422597 4/1973 United Kingdom .
2021765 2/1979 United Kingdom .

OTHER PUBLICATIONS

Z. Anal. Chem. 264, pp. 105-109 (1973); Springer Verlag.
Spectrachimica Acta, vol. 30B, pp. 169-177, Pergamon Press.
Atomic Absorption Newsletter, pp. 109-113: Automated Injection Method for Dispensing Small Volume Samples in Flame Atomic Absorption, Y. H. Berndt and E. Jackwerth.
Atomic Absorption Newsletter, 1978, pp. 113-114: A Simple Teflon Sampling Manifold for Use with Small Injections, by A. Eaton and E. Schiemer.

Primary Examiner—F. L. Evans
Attorney, Agent, or Firm—Karl F. Ross

[57] ABSTRACT

A dosing device for emitting liquid samples to an automatic absorption spectrophotometer having a liquid atomizer for the samples, utilizes at least one three-way distributor, one of the ports of which communicates with the atomizer, another port of which communicates with the spectrophotometer, and a third part of which communicates with a vessel containing the liquid sample. An electromagnetic valve is provided for the port communicating with the atmosphere. In the preferred embodiment, two such distributors are provided in series and the second distributor is connected to a source of pure solvent and is interposed between the first distributor and the spectrophotometer.

4 Claims, 3 Drawing Figures

DEVICE FOR PULSE DOSAGE OF LIQUID MICROSAMPLES INTO THE FLAME OF ATOM ABSORPTION SPECTROPHOTOMETER

FIELD OF THE INVENTION

This invention relates to a device for pulse dosage of liquid microsamples into the flame of an atom absorption spectrophotometer (AAS).

BACKGROUND OF THE INVENTION

Devices for pulse dosage of liquid microsamples into the flame of an AAS are known, which have a polytetrafluoroethylene funnel which is connected to the unit for spraying the sample by means of a special capillary. The dosage of the solution in volumes of 50-100 microliters is performed manually, using microliter pipettes provided with special movable plastic nozzles (1).

Another known device for automatic pulse dosage of liquid microsamples into the flame of an AAS has been constructed based on the studies performed by Berndt and Jackwerth and is used by Perkin Elmer. It consists of a combination of a Teflon funnel provided with a microliter pipette and a small pump, a system for circular step moving of a table upon which beakers containing samples to be tested are laid. The operation of the device depends on the electronics of the atom absorption spectrophotometer. It permits an automatic dosage of samples of volumes of 50 or 100 microliters.

A manual-acting device for pulse dosage is known, which has a small container with a conical bottom. The sample of a preliminary known volume of 50-500 microliters is pumped only once by the capillary, said capillary being connected to the pulverizer of the AAS.

It is a common disadvantage of the well known automatic devices that these are extemely expensive.

In manual-acting devices for pulse dosage, relatively high cost microliter pipettes with replaceable nozzles are used and the dosage is both unconvenient and tiresome when a large number of samples are to be tested, which results in a lower reproducibility.

OBJECT OF THE INVENTION

The object of this invention is to provide a device for pulse dosage of liquid microsamples into the flame of an atom absorption spectro photometer, said device being such as to enable a simple, fast, reliable, precise and convenient handling of the samples with both good reproducibility and low cost.

SUMMARY OF THE INVENTION

This object is attained by a device, which includes a distributor and an electromagnetic valve and is constructed of two units at most, said units being located at different levels with respect to the pulverizer (liquid sample atomizer) of the atom absorption spectrophotometer, and a three way distributor connected to an electromagnetic valves is used; the three-way distributor of the higher level unit is connected to a container for the sample as well as to the atmosphere through an electromagnetic valve and to the pulverizer of the atom absorption spectrophotometer through the three-way distributor of the lower level unit, said distributor of the lower level unit being connected also to a container for the sample solvent.

In a second embodiment of the device, only one unit is used and its electromagnetic valve is connected to the atmosphere and its three-way distributor is connected directly to the pulverizer of the atom absorption spectrophotometer.

In a third embodiment of the device, only one unit is used, where its electromagnetic valve is connected to a container for the sample solvent and its three-way distributor is connected directly to the container for the sample under test.

Each of the three-way distributors is provided with a channel, which connects it with the electromagnetic valve, the channel being connected to a through-hole including an angle of between 15° and 165° with said channel. The through-hole can be of a constant cross section or a cross section which is variable (e.g. stepped).

The device according to the invention possesses the following advantages: there is no need for microliter pipettes; dosed volumes can be smoothly varied starting from 50 microliters to a continuous flow; it is possible to work in a mode of integration of the signals at a minimal volume with zeroing in the flame according to the respective solvent used, followed by a pulse dosage of a microsample in the same solvent, a continuous dosage of the solvent and pulse dosage of the sample, thereby maintaining the flame stoichiometry and ensuring simplicity, convenience, reliability, speed and exactness in operation. Moreover, the device is readily available and of low cost.

SPECIFIC DESCRIPTION

Figure 1:
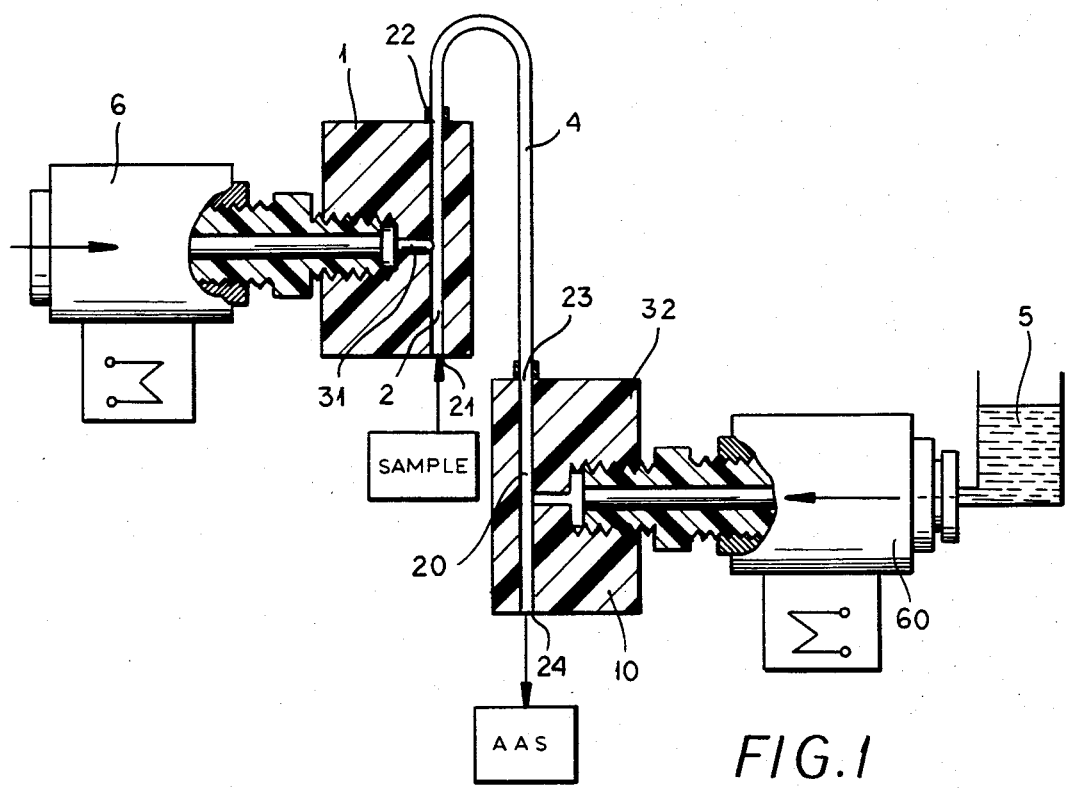
FIG. 1 is an elevational view of the dosing apparatus of the invention partly broken away.

FIG. 1 is a diagram of the device for pulse dosage of liquid microsamples into the flame of an AAS, which consists in two units located at different levels over an AAS pulverizer, where three-way distributors connected to electromagnetic valves are used. The three-way distributor 1 of the higher level unit is connected to a container for the sample by means of an opening 21 at the through-hole 2 as well as to the atmosphere by means of an electromagnetic valve 6 through the channel 31 and opening 22 at the through-hole 2, using the tube 4 provided with the opening 23 at the through-hole 20 of the three-way distributor 10 pertaining to the lower level unit, said three-way distributor 10 being connected both to a container 5 for the sample solvent by means of the lower level unit electromagnetic valve 60 through the channel 32 and to the pulverizer of the AAS by means of the opening 24 at the through-hole 20.

There is an angle of 90° concluded between the through-holes 2 and 20 in the three-way distributors 1 and 10 and the channels 31 and 32 provided for connection with the corresponding electromagnetic valves.

The device operates as follows: The flame of the AAS is ignited. Both electromagnetic valves 6 and 60 are opened. The pure solvent contained in the container 5 passes through the electromagnetic valve 60, channel 32, opening 24 and by means of a plastic tube enters the pulverizer (or, respectively, flame of the AAS). A portion of the solvent is ascended along the plastic tube 4, thereby forming a hydraulic seal against the air inlet from the electromagnetic valve 6. No suction of solution of the liquid sample occurs. Thus, zeroing of the apparatus takes place under said conditions. A higher rate of solvent admission is ensured compared with the liquid consumption of the pulverizer due to the higher level of the container 5 compared with the level of the pulverizer and by the proper choice of the cross sections of channels 32 and 2.

The two electromagnetic valves 6 and 60 are closed during a short strictly defined time by means of electromagnetic relays actuated by a signal, submitted by the operator. The dosage of pure solvent stops in the manner described above. The liquid sample is pumped and enters the AAS pulverizer through a plastic tube after being passed through a plastic tube, the opening 21, the through-hole 2, the opening 22, the plastic tube 4, the opening 23, the through-hole 20 and opening 24. Pulverization of the pure solvent is restored after the opening of the electromagnetic valves 6 and 60. The amount of volumes being dosed is controlled by the duration of the closure time of the electromagnetic valves.

The device permits a continuous dosage of the solvent and pulse dosage of the sample, i.e. sample-solvent-sample . . . without any air feeding, which results in an improvement of the flame parameters or, respectively, efficiency of the atomization of a number of elements, while ensuring the possibility one to work without deuterium correction.

Results obtained using the above outlined device are given in Table 1.

Figure 2:
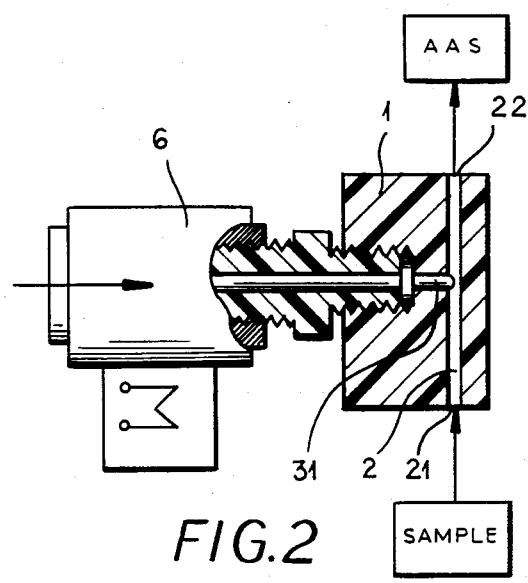
FIG. 2 is a fragmentary cross sectional view illustrating the distributor according to another embodiment of the invention.

FIG. 2 is a diagram of a device for pulse dosage of liquid microsamples into the flame of AAS, said device being constructed of a single unit. The three-way distributor 1 of said unit connects with the atmosphere by means of a channel 31 and electromagnetic valve 6; with the container for sample under test by means of the opening 21 at the through-hole 2 and directly with the pulverizer of the AAS by means of the opening 22 at the through-hole 2.

This device operates as follows. The opening 22 is connected to the pulverizer of the AAS by means of a plastic tube. Then, the control panel of the electromagnetic valve 6 is switched on. The flame of AAS is ignited. Zeroing of the apparatus can be made either on the flame or corresponding solvent used.

A signal submitted by the operator closes the electromagnetic valve for a short strictly defined time, said time being controlled by electronic timers. The air access to the through-hole 2, coming from the electromagnetic valve 6 through the channel 31, is disconnected. The solution of the sample under test is pumped for a short time and passes through: a plastic tube, the opening 21, the through-hole 2, the opening 22 and then, by means of a plastic tube enters the pulverizer of AAS. Thus, pulse dosage of liquid microsamples is accomplished, which stops at the moment of opening of the electromagnetic valve 6, i.e. a dosage of the type sample-air-sample . . . is performed. The amount of the volumes being dosed is determined by the closure time of the electromagnetic valve 6.

Results obtained using the above said device are given in Table 2.

In a third version of the device embodiment, the device consists in a single unit. The three-way distributor 10 of said unit is connected to a container 5 for the sample solvent, to the electromagnetic valve 60 and channel 32, to a container for the sample under test by means of the opening 23 at the through-hole 20 and to the pulverizer of AAS by means of the opening 24 at the same through-hole 20.

Figure 3:
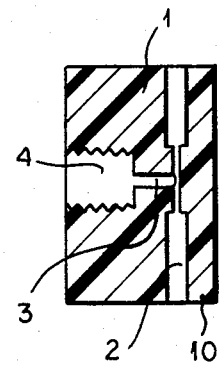
FIG. 3 is an axial section through another distributor according to the invention.

In all possible versions of embodiment of the device, the through-holes 2 and 20 can be of either constant (FIGS. 1, 2) or step variable (FIG. 3) cross sections.

TABLE 1

Relative absorption from 15 measurements performed over solutions in the flame of AAS after a pulse dosage of the type sample solvent-sample . . . using the device according to the invention.

| ELEMENT | CONCENTRATION $mkg.ml^{-1}$ | SOLVENT | A | SR % |
|---|---|---|---|---|
| Cu | 2.0 | MMK | 0.147 | 5.32 |
|  | 10.0 | $H_2O$ | 0.197 | 2.26 |
| Cd | 0.4 | MMK | 0.141 | 2.24 |
|  | 4.0 | $H_2O$ | 0.248 | 3.32 |
| Te | 4.0 | MMK | 0.224 | 6.29 |
|  |  | $H_2O$ | — | — |
| Pb | 10.0 | MMK | 0.518 | 0.70 |
|  | 10.0 | $H_2O$ | 0.095 | 5.20 |
| Fe | 4.0 | MMK | 0.284 | 1.42 |
|  | 4.0 | $H_2O$ | 0.042 | 6.47 |
| Al | 50.0 | xylene | 0.280 |  |
|  | 50.0 | $H_2O$ | 0.300 |  |
| Sn | 50.0 | MIBK | 0.790 |  |
|  | 50.0 | $H_2O$ | 0.120 |  |

MMK = methylmethalcrylate
MIBK = methyiisobutyl ketone

Organic solutions of Cu, Cd, Te and Pb are obtained by extraction of the diethyldithiocarbamate complexes of Cu, Cd, Te and Pb with methylmethacrylate. The Fe is extracted as a hydrochloric acid complex, and the Sn and Al are extracted as standard caproate solutions.

TABLE 2

Absorption of solutions in the flame of AAS, measured after pulse dosage of the type sample-air-sample . . .

| DEVICE ACCORDING TO THE INVENTION | max—324.7 nm split-0.7 Cu-1.5 mkg. $ml^{-1}$ | | max—228.8 nm split-0.7 Cd-0.4 mkg $ml^{-1}$ | | max—217.0 nm split-0.7 Pb-5.0 mkg. $ml^{-1}$ | |
|---|---|---|---|---|---|---|
|  | A | SR % | A | SR % | A | SR % |
| aqueous device | 0.065 | 1.58 | 0.032 | 7.08 | 0.093 | 1.65 |
| solutions funnel P.E. | 0.058 | 4.33 | 0.027 | 9.48 | 0.074 | 4.88 |
| solutions device | 0.253 | 0.66 | 0.127 | 2.82 | 0.076 | 4.60 |
| MIBK funnel P.E. | 0.256 | 0.86 | 0.100 | 3.28 | 0.081 | 5.04 |
| solutions device | 0.221 | 1.18 | 0.107 | 3.53 | 0.061 | 5.67 |
| MMK funnel P.E. | 0.220 | 1.18 | 0.105 | 3.68 | 0.062 | 7.50 |
| solutions device | 0.118 | 1.73 | 0.084 | 7.88 | — | — |
|  | 0.108* | 0.91 | — | — | — | — |

TABLE 2-continued

| | Absorption of solutions in the flame of AAS, measured after pulse dosage of the type sample-air-sample... | | | | | |
|---|---|---|---|---|---|---|
| | max−324.7 nm split-0.7 | | max−228.8 nm split-0.7 | | max−217.0 nm split-0.7 | |
| DEVICE ACCORDING | Cu-1.5 mkg. ml$^{-1}$ | | Cd-0.4 mkg ml$^{-1}$ | | Pb-5.0 mkg. ml$^{-1}$ | |
| TO THE INVENTION | A | SR % | A | SR % | A | SR % |
| TOLUENE funnel P.E. | 0.126 | 1.92 | 0.048 | 7.68 | — | — |

*zeroing performed on organic solvent. In other cases, zeroing is accomplished based on the flame.
MIBK = methylisobutyl ketone
MMK = methylmethacrylate
SR % = relative standard shift Absorption values are average of 25 measurements (II).

We claim:

1. In an atomic absorption spectrophotometer provided with a flame liquid sample atomizer, and a source of a liquid sample to be analysed, the improvement which comprises:
   a three-way distributor having a throughgoing passage interconnecting a pair of ports, and a further passage opening into said throughgoing passage between said pair of ports;
   means connecting one of the ports of said pair to said source;
   means for connecting the other port of said pair to said atomizer;
   an electromagnetic valve connected to said further passage for admitting air through said further passage to said throughgoing passage, the means connecting said other port to said atomizer including a second three-way distributor having a throughgoing passage communicating between said other port and said atomizer and a further passage opening into said throughgoing passage, communicating with a supply vessel for a solvent and provided with a second electromagnetic valve for closing the further passage, said second distributor being located at a level below the first distributor.

2. The improvement defined in claim 1, wherein said further passage includes an angle with a respective throughgoing passage of the respective distributor between 15° and 165°.

3. The improvement defined in claim 1 wherein said throughgoing passage has a stepped cross section.

4. In an atomic spectrophotometer provided with a liquid sample atomizer, and a source of a liquid sample to be analysed, the improvement which comprises:
   a three-way distributor having a throughgoing passage connecting said source to said atomizer, and a further passage opening into said throughgoing passage,
   a supply vessel for a solvent connected with said further passage; and
   an electromagnetic valve connected to said further passage and said vessel for controlling the feed of solvent from said vessel to said throughgoing passage.

* * * * *